United States Patent
Borchers

(10) Patent No.: US 7,728,960 B2
(45) Date of Patent: Jun. 1, 2010

(54) MACHINE AIDED COMBINATION OF AN NIR MATERIAL CONCENTRATION MEASUREMENT WITH A TEMPERATURE PROFILE MEASUREMENT BASED ON FIBER BRAGG GRATINGS IN OPTICAL FIBERS

(75) Inventor: Wolfgang Borchers, Köln (DE)

(73) Assignee: Bayer Technology Services GmbH, Leverkusen (DE)

( * ) Notice: Subject to any disclaimer, the term of this patent is extended or adjusted under 35 U.S.C. 154(b) by 55 days.

(21) Appl. No.: 11/814,030

(22) PCT Filed: Jan. 17, 2006

(86) PCT No.: PCT/EP2006/000357

§ 371 (c)(1),
(2), (4) Date: Jul. 16, 2007

(87) PCT Pub. No.: WO2006/079466

PCT Pub. Date: Aug. 3, 2006

(65) Prior Publication Data

US 2008/0088822 A1    Apr. 17, 2008

(30) Foreign Application Priority Data

Jan. 28, 2005  (DE) ............... 10 2005 003 989
Jan. 28, 2005  (DE) ............... 10 2005 004 293
Mar. 5, 2005   (DE) ............... 10 2005 010 216

(51) Int. Cl.
*G01N 21/00*    (2006.01)

(52) U.S. Cl. .............................. 356/73; 356/51; 356/478
(58) Field of Classification Search ................... 356/73, 356/478, 477, 479, 451, 51
See application file for complete search history.

(56) References Cited

U.S. PATENT DOCUMENTS

| | | | |
|---|---|---|---|
| 6,228,650 B1 | 5/2001 | Moore et al. | |
| 6,300,633 B1 | 10/2001 | Hunt et al. | |
| 2004/0010170 A1 | 1/2004 | Vickers | |
| 2005/0003553 A1 | 1/2005 | Mahrenholts et al. | |

FOREIGN PATENT DOCUMENTS

DE    103 22 439 A1    12/2004

OTHER PUBLICATIONS

Kersey A. D.,et al,: "Fiber Grating Sensors" Journal of Lightwave Technology, IEEE Service Center, New York, NY US, vol. 15, No. 8, Aug. 1997, pp. 1442-1462, XP0000720469 ISSN: 0733-08725.
Alan D. Kersey,Michael A, Davis, Heather J. Patrick, Michael LeBlanc, K.P. Koo, C.G. Askins, M. A., Putnam and E. Joseph Friebele. Fiber Grating Sensors,Lightwave Technology, Journal of vol. 15, Issue 8, Aug. 1997 pp. 1142-1463.
K. O. Hill, Y. Fujii, D. C. Johnson, and B .S. Kawasaki, Applied Physics Letters, May 15, 1978, vol. 32, Issue 10, pp. 647-649.

*Primary Examiner*—Hwa S. A Lee
(74) *Attorney, Agent, or Firm*—Norris McLaughlin & Marcus, PA; Christa Hildebrand, Esq.

(57) ABSTRACT

The invention relates to a spectroscopic arrangement and a method for combining devices for measuring material concentrations NIR associated with a spectroscopic evaluation of glass fiber and fitted with fibers Bragg gratings (FBG) for measuring temperature profiles.

8 Claims, 9 Drawing Sheets

MACHINE AIDED COMBINATION OF AN NIR MATERIAL CONCENTRATION MEASUREMENT WITH A TEMPERATURE PROFILE MEASUREMENT BASED ON FIBER BRAGG GRATINGS IN OPTICAL FIBERS

This is an application filed under 35 USC §371 of PCT/EP2006/000357.

BACKGROUND OF THE INVENTION

The present invention relates to a method for machine aided combination of NIR material concentration measurements with the spectroscopic evaluation of glass fibers, fitted with fiber Bragg gratings (FBGs) for measuring temperature profiles.

It is customary to use Fourier transform near-infrared (FT-NIR) spectrometers for online measurement of material concentrations in complex material mixtures in chemical pharmaceutical plants (see PROCESS, April 2003 "Bessere Daten für effizientere Prozesse" ["Better data for more efficient processes"]. These units are currently to be found in processing designs having optical multiplexers for the operation of a number of optical probes (for example from Bruker, Matrix-F). The essential optical components are integrated in these spectrometers (light source, interferometer, detector, reference laser for the wavelength calibration of the interferometer). In order to obtain a good signal-noise ratio, use is made for process coupling of multimode glass fibers (MM glass fibers) with a large light-carrying cross section (several 100 µm). The spectrometers themselves are of high resolution and cover a large spectral bandwidth (approximately 800 nm to 2.5 µm).

As regards temperature profile measurement by means of FBG fitted glass fibers [see DE 0403132404 A and, for FBG technology see R. Kashyap, "Fiber Bragg Gratings", Academic Press, 458 (1999), www.inventivefiber.com.sg/FBG.html, K. O. Hill et al:, Appl, Phys. Lett. 32, page 647 (1978)], which is already based in principle on the use of comparatively optically weak single mode glass fibers (SM glass fibers), the optical components have decidedly different properties than in the case of the material concentration measurement via FT-NIR spectroscopy. Since the application of FBG technology resides originally and to a greatly predominant extent in optical telecommunication, the corresponding optical components are also specifically tuned to the requirements of this technology. Usually narrowband, high-resolution diode array spectrometers or scanning laser light sources or fiber spectrometers are used. The light sources are adapted to the spectrometers (SLEDs (Superluminescent Light-Emitting Diode) or scanning laser sources), and have typical bandwidths of a few tens of nanometers.

The two technologies (FT-NIR for determining material concentration and spectroscopy on FBG fitted glass fibers) have an overlap in the spectral region used and in the possible application in chemical-pharmaceutical apparatuses, in apparatuses of petrochemistry, in particular refineries, and in apparatuses of the food processing industry (Reactors, columns (for example for distillation, extraction or for drying), crystallizers, dryers, furnaces, specifically microwave-heated or induction furnaces). This points to the need for a common equipment basis.

Starting from the prior art, the object therefore was that of modifying the optical components and/or their assembly such that the two measuring probes (process light barriers for concentration measurements and FBG fitted glass fibers for temperature measurements) can be operated using the same equipment basis, preferably optical multiplexing.

BRIEF SUMMARY OF THE INVENTION

The machine-based combination of FT-NIR spectroscopy with the spectroscopic evaluation of FBG fitted glass fibers is nowhere mentioned in the prior art.

It has surprisingly been found that combined spectroscopy is possible on material mixtures and on FBG fitted glass fibers with the aid of a specific configuration of the optical components and, in some circumstances, with the use of specific additional light sources. The units, glass fibers etc. sufficiently well known from the prior art and commercially available (see above prior art) can be used in this case to carry out the present invention.

The spectroscopic arrangement according to the invention therefore consists of at least one light source for FBG fibers and an NIR measuring cell, at least one optical multiplexer for connecting the measuring section to the spectrometer, at least one FBG fiber and at least one glass fiber for NIR spectroscopy, an interferometer, a detector and a signal evaluation/control unit, it being possible for some of these components also to have already been combined in more complex components (for example FT-NIR spectrometer).

It is therefore now possible to use only one spectrometer to conduct two measurement tasks of different type on apparatuses in the chemical-pharmaceutical industry. Owing to the capacity for optical multiplexing, one spectrometer can be used to conduct a number of measurement tasks, in particular even ones of different type, in a quasi-simultaneous fashion. This is a substantial contribution to cost reduction for the individual measuring point, the more so as there is also only the need to access the process control system once. It can be entirely sensible in this case to use the inventive combination of apparatuses even when the measurement of material concentrations and the measurement of temperatures with the aid of fiber Bragg gratings take place in various apparatuses.

The particular advantage of this method for FBG temperature measurement—owing to the large spectral acceptance of the analyzer and to the spectrally wide light source—is also that the spectral distribution of the FBGs can be performed on a glass fiber strand with relatively large spectral spacings such that the possible spectral change caused by temperature changes does not lead so quickly to a spectral overlap with another FBG on the fiber. Alternatively or else in supplementary fashion, this advantage can also be used in order to write more FBGs onto a fiber without the individual spectra on the FBGs overlapping in the case of temperature variations.

DETAILED DESCRIPTION OF THE INVENTION

Figure 1:
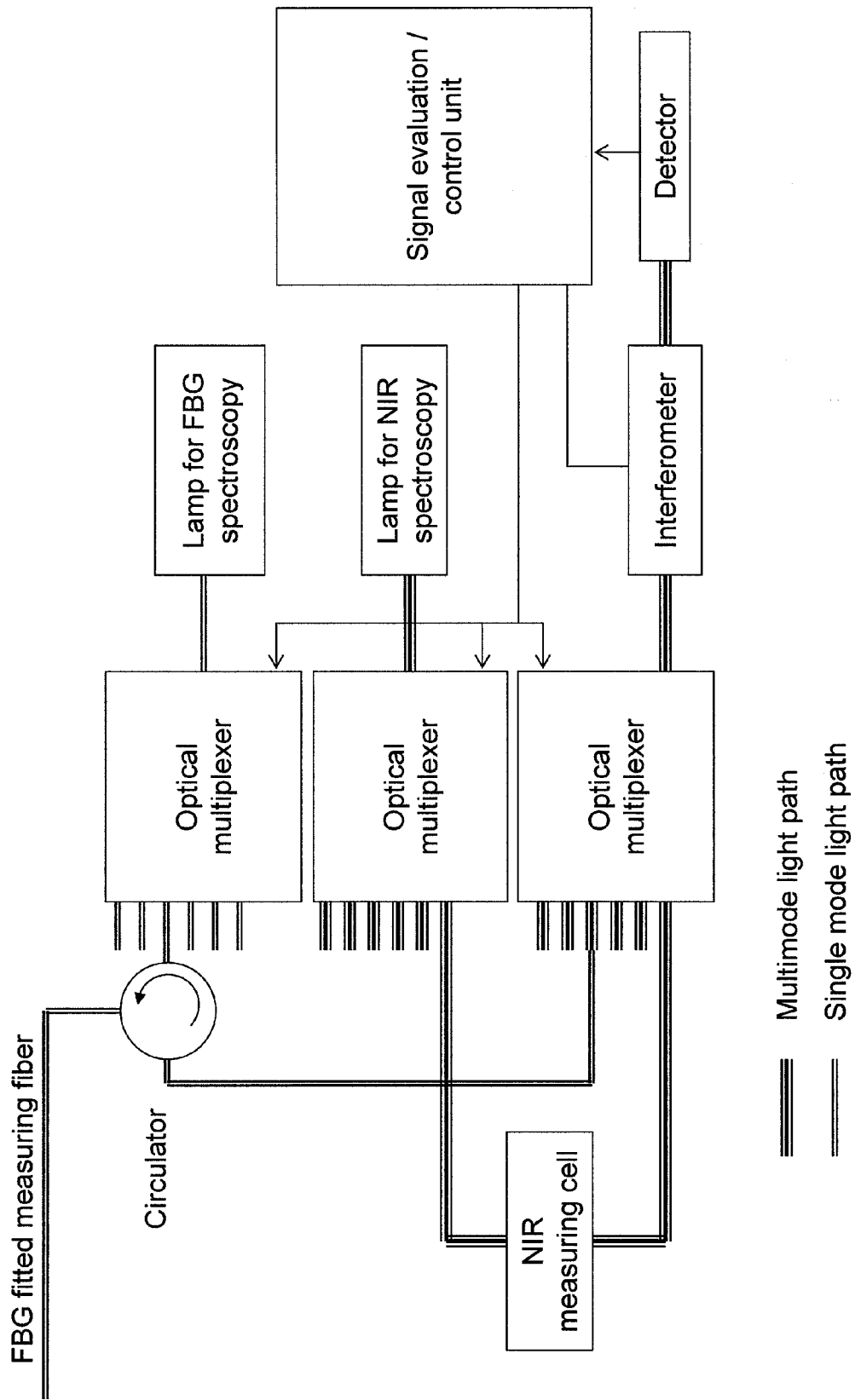
FIG. 1 illustrates a schematic illustration of the overall spectroscopic design.

According to the method of the invention, an FT-NIR spectrometer is used in an arrangement as illustrated in FIG 1. The interferometer is located in the optical path between circulator and detector. It is possible in this way to construct a separate illumination path for each of the two spectroscopic methods with the aid of components that are optimum for the respective spectroscopy. By contrast with the customary equipping of multichannel FT-NIR spectrometers with two multimode multiplexers operated in synchronized fashion, the method according t the invention provides an additional single mode multiplexer that is likewise operated in a synchronous fashion with the two other multiplexers. The interconnection of the multiplexers is controlled in this case such that the measuring channel connected to the input of the interferometer can also be supplied with the corresponding light source. The total number of possible measuring sections (NIR measuring probes and FBG fitted glass fibers, respectively) is limited in this case only by the number of the input channels of the multiplexer upstream of the input of the interferometer.

Use may be made for the light sources intended for NIR spectroscopy (determination of material concentration) of the sources customary there (for example halogen lamps) with corresponding coupling into the MM glass fibers, and/or also of direct coupling to the optical multiplexer with MM glass fiber coupling at the outputs of the multiplexer.

For the spectroscopy on the FBG fitted glass fibers, use may be made of the broadband light sources specifically customary therefor (for example ELEDs or SLEDs with fiber pigtail). These light sources are, however, restricted to a few 10 nm in the useable emission bandwidth.

The person skilled in the art does not expect here that the light intensity that can be achieved by means of an SM glass fiber is sufficient for analyzing by means of FT-NIR spectroscopy. FT-NIR spectrometers are usually operated with the substantially higher intensities that can be achieved in MM glass fibers: it is therefore a complete surprise that even the low intensities possible in SM glass fibers are sufficient for operating the spectrometers and enable the combined operation according to the invention.

It has, moreover, surprisingly been found that sufficient light is available for the detector of the FT-NIR spectrometer even with the aid of conventional incandescent lamps, in particular halogen lamps, and a high intensity condenser, which focuses the light onto the end face of an SM glass fiber, instead of the ELEDs and/or SLEDs. The reason why this is so astonishing is that the difference in the coupling efficiency between MM glass fiber and SM glass fiber turns out to be smaller by approximately the factor of 20 000 in the case of the SM glass fiber than in the case of the MM glass fiber (geometric difference in the cross sectional area and difference in the numerical aperture). It is therefore possible in a preferred embodiment to operate both the NIR spectroscopy and the FBG temperature measurement with the aid of a common light source that is coupled in differently depending on requirement.

Figure 2:
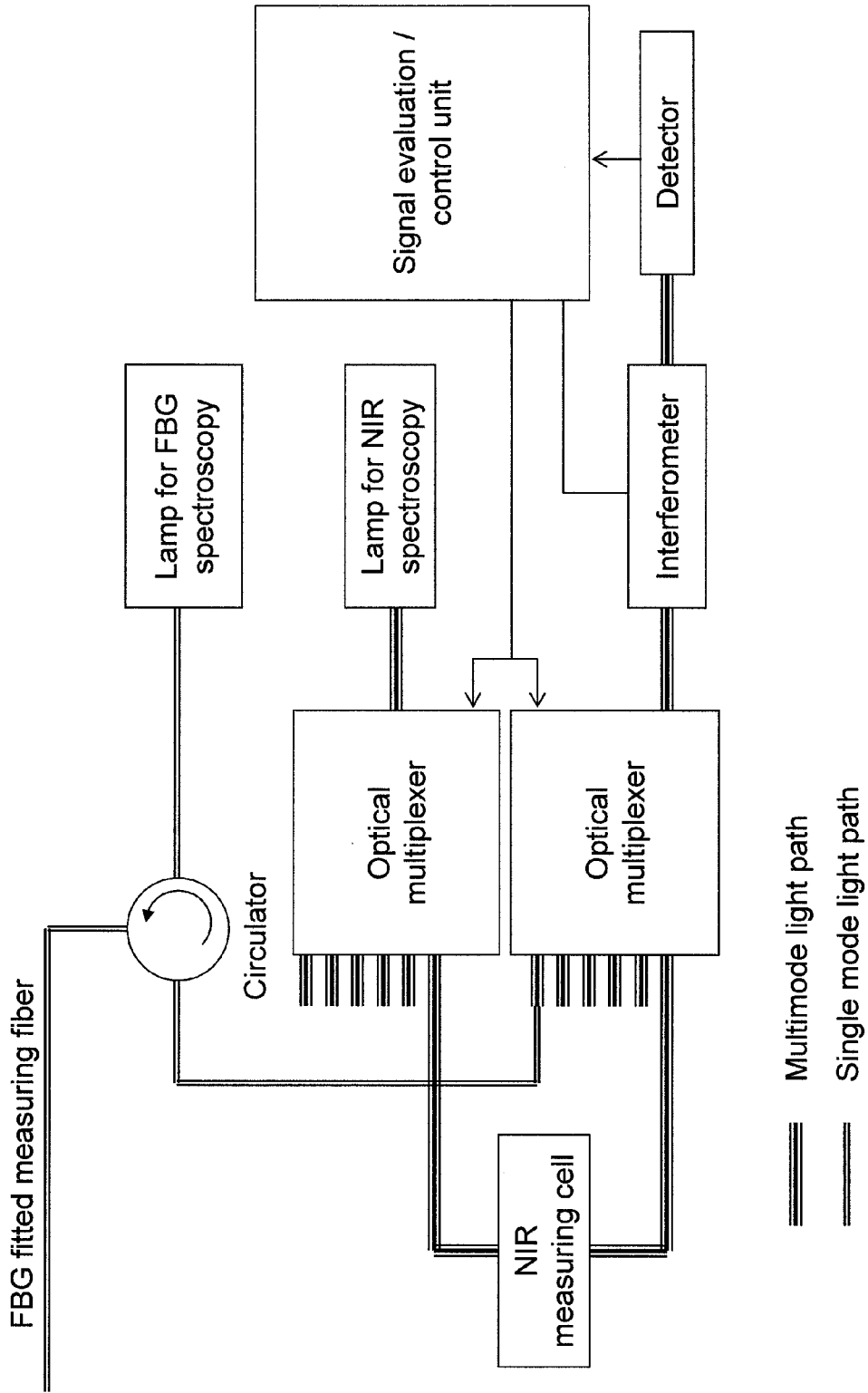
FIG. 2 illustrates an exemplary schematic illustration of the spectroscopic arrangement without SM glass fiber multiplexer in the case of use of only one FBG measuring fiber.

As an alternative to the abovementioned procedure, it is also possible to dispense with one or even all multiplexers for switching over the light source(s) when each unit (FBG fitted fiber or NIR measuring cell) to be examined spectroscopically is supplied with a dedicated, suitable light source. This can be sensible (FIG. 2) from financial considerations, or because only one measuring section (FBG fitted fiber or NIR measuring cell) of the respective type is being operated. This possibility can, however, also be used specifically in order to select specifically fitting light sources for various FBG fitted glass fibers.

In one variant, separate light sources are optionally connected to each measuring section with the aid of respectively suitable multiplexers. Also preferred is an embodiment in which the FBG spectroscopy is carried out from only one end of the fiber.

The temporal sequence of the measuring sections to be examined spectroscopically can preferably be freely selected by the equipment controller.

In a particularly preferred embodiment, it is, moreover, possible to measure the FBG spectroscopy optionally in reflection or transmission.

Figure 3:
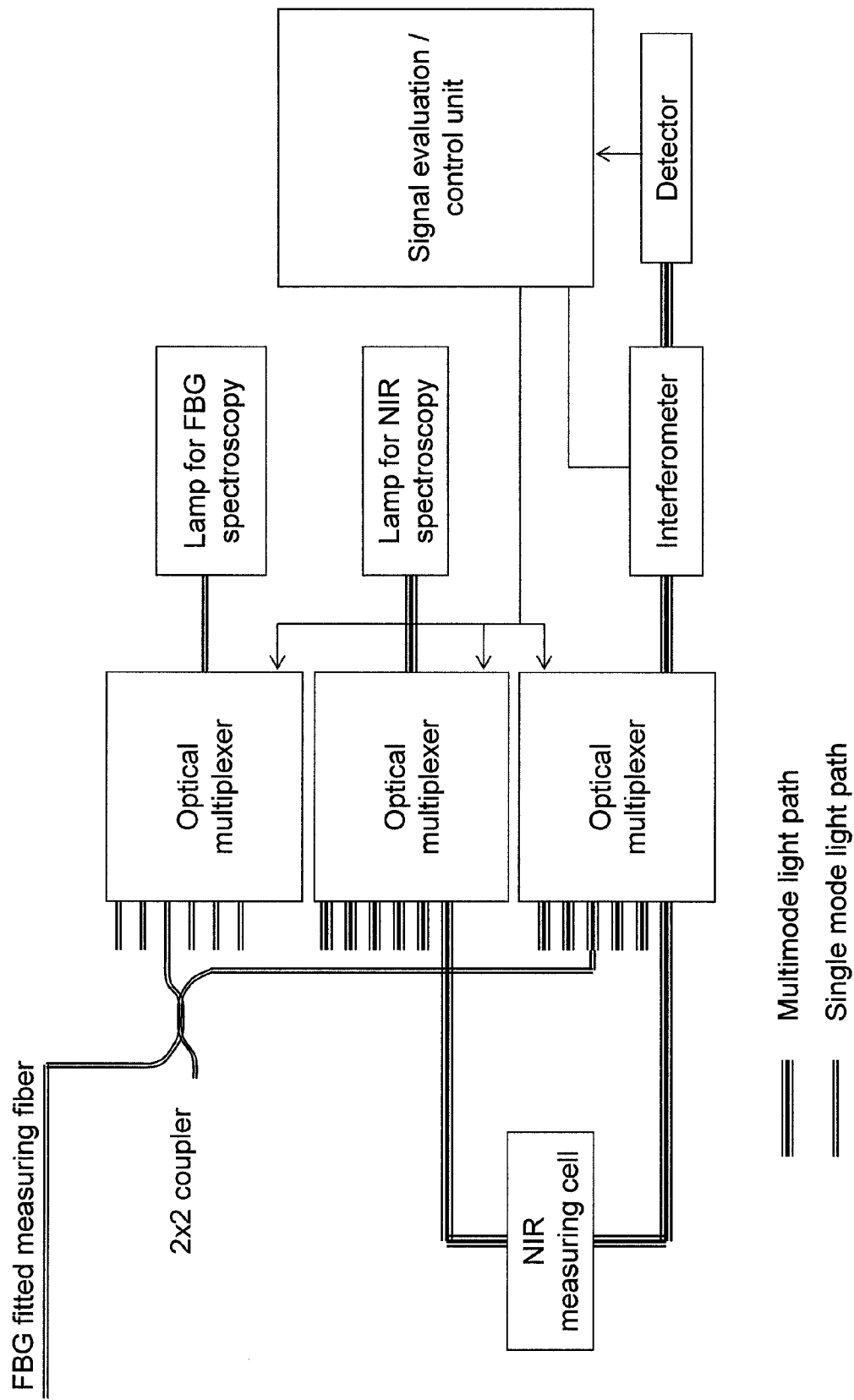
FIG. 3: Exemplary illustration in the case of use of a 2×2 coupler instead of a circulator.

In a further variant, the circulator of one or more measuring sections of FBG fitted glass fibers can be replaced by a 2×2 coupler. This combination is, however, generally associated with larger losses in intensity (FIG. 3). However, it can nevertheless prove to be advantageous when there is a need to cover a large spectral width for which the increasing attenuation of the circulators in the spectral edge region exceed the losses of a 2×2 coupler.

Figure 4:
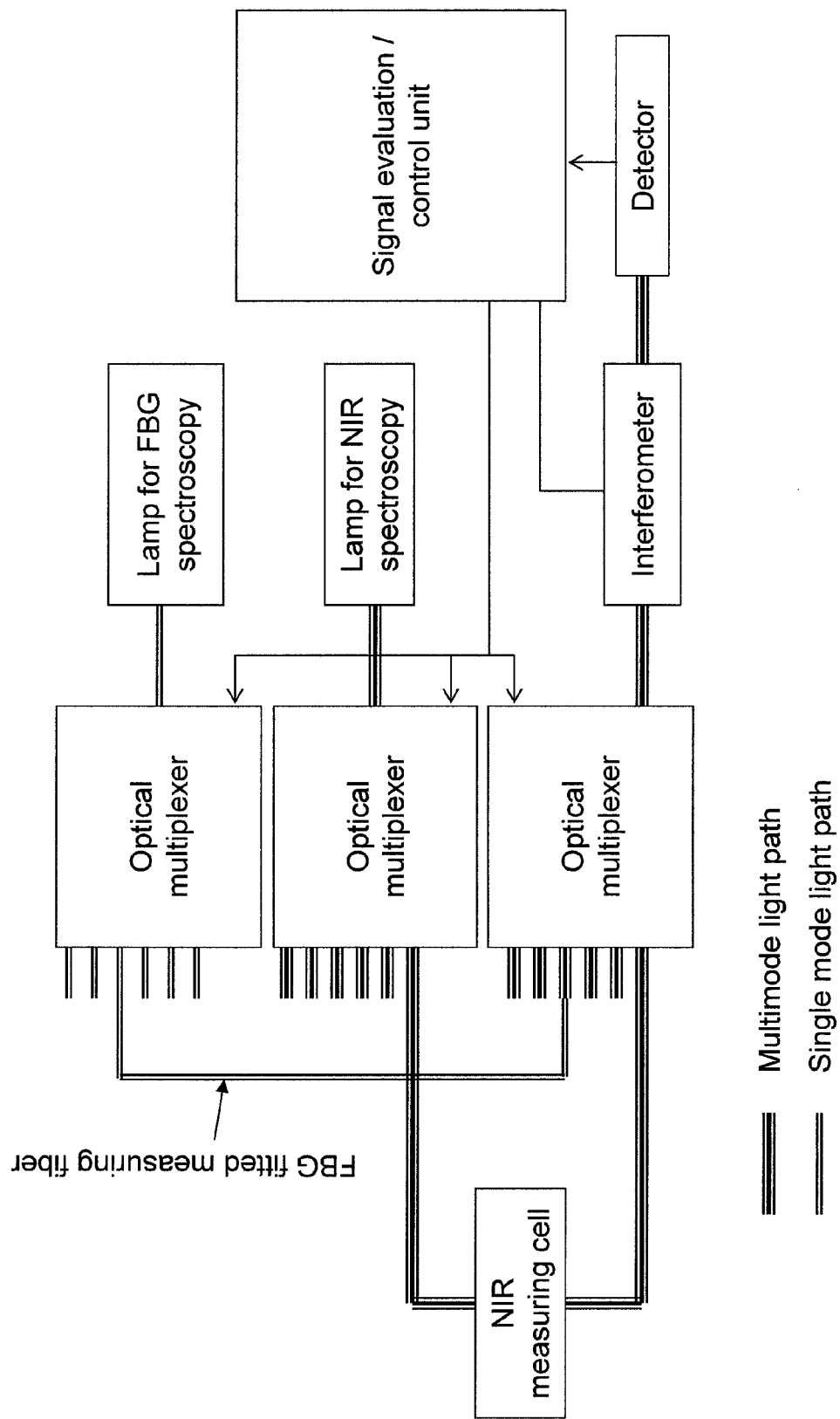
FIG. 4 Exemplary illustration for transmission spectroscopy on a measuring fiber fitted with fiber Bragg gratings.

In a further variant, the FBG fitted measuring fiber for one, or also several measuring sections can be connected directly, without the use of a circulator or 2×2 coupler, into the light path between illuminating fiber and input multiplexer of the interferometer, and thus be evaluated in transmission (FIG. 4). However, this is not the preferred variant for temperature evaluation of the FBG spectra, since the latter exhibits asymmetries in this arrangement.

Figure 5:
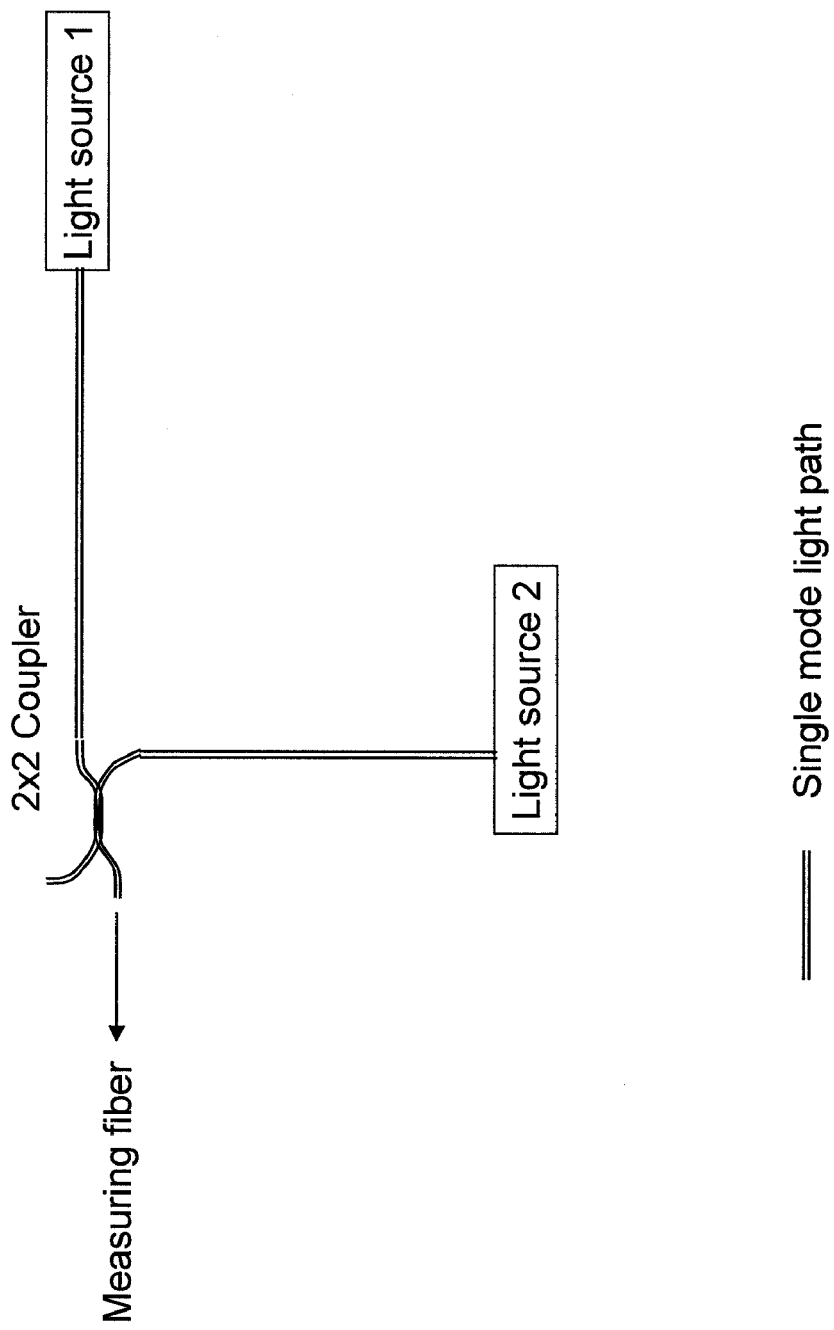
FIG. 5 Combination of two light sources for spectroscopy on glass fibers fitted with fiber Bragg gratings.

In a further variant, a number of light sources are coupled to one another by a 2×2 coupler for spectroscopy on glass fibers fitted with fiber Bragg gratings (FIG. 5). It is possible in this way to extend the effective spectral illumination bandwidth. This principle can also be cascaded for more than two light sources. This spectral combination of a number of light sources is likewise a preferred embodiment.

In a likewise preferred embodiment, a common data path to the process control system is used for the measurement of material concentrations and temperature and/or temperature profiles.

The spectroscopic arrangement according to the invention can be used in various processes in the food industry, the food processing industry, the chemical-pharmaceutical industry and in petrochemistry, in particular refineries, in order to determine appropriate data. The spectroscopic arrangement according to the invention is suitable as measuring device in every process technology construction of these industries in which it is necessary or appears useful to measure material concentrations and/or temperature and/or temperature profiles.

Embodiments that make use of the parameters, connections, definitions and explanations named as preferred, particularly preferred or very particularly preferred are preferred, particularly preferred or very particularly preferred.

The definitions, parameters, connections and explanations set forth in general in the description or set forth in preferred ranges can, however, also be combined with one another at will, that is to say between the respective ranges and preferred ranges.

The following examples are intended to illustrate the present invention but without restricting it:

EXAMPLES

Figure 6:
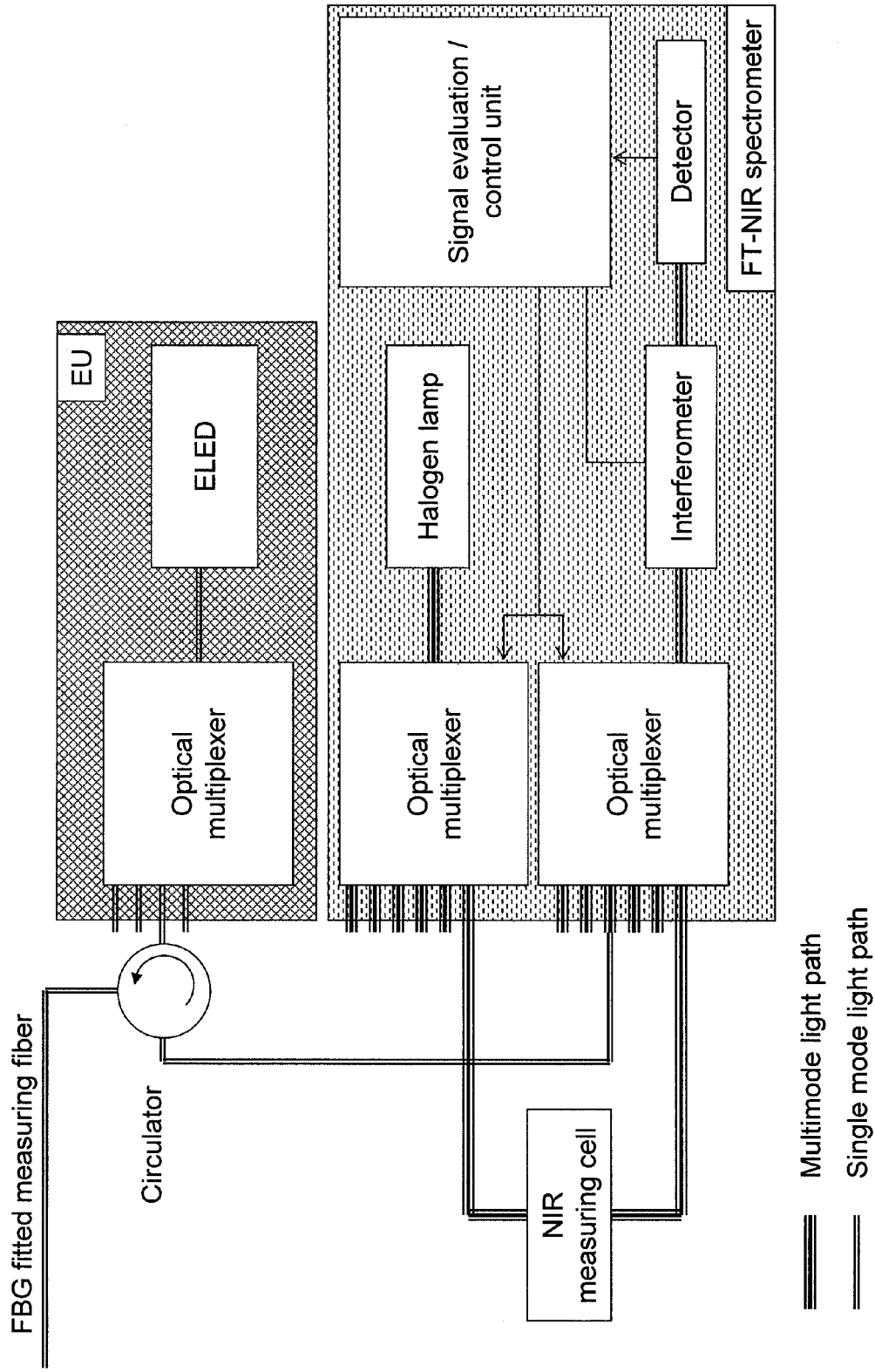
FIG. 6 Exemplary configuration for spectroscopy on glass fibers fitted with fiber Bragg gratings.
Figure 8:
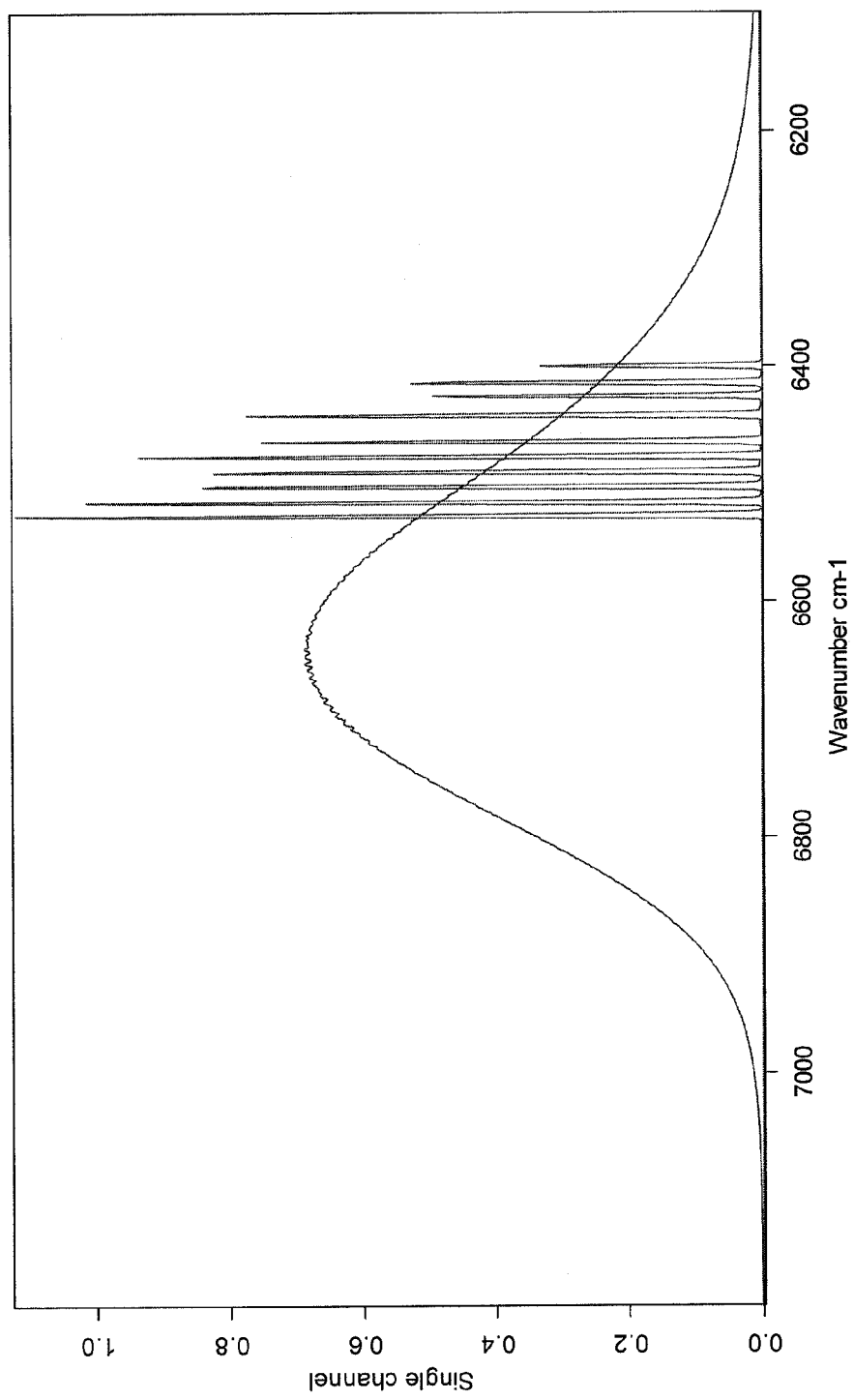
FIG. 8 Reflection spectrum of a glass fiber fitted with ten fiber Bragg gratings, recorded with the aid of a Bruker Duplex FT-NIR spectrometer; the intensity distribution of the light source used from the EU supplied by AOS is likewise illustrated.

FIG. 6 illustrates an arrangement for machine-based combined spectroscopic evaluation of NIR probes and fiber Bragg gratings for temperature measurement. The ELED with a downstream optical MEMS multiplexer from an FBG evaluation unit (EU) supplied by AOS, Dresden is used for the light source for the fiber Bragg grating evaluation. The fiber Bragg gratings were written into an SMS-28 fiber, likewise from AOS. The type CIR-3-2-2-10-FA from Opneti was used for the circulator. The Matrix Duplex machine from Bruker was used in the illustrated configuration as FT-NIR spectrometer. The spectrum of the fiber Bragg grating measured therewith is illustrated in FIG. 8.

Figure 7:
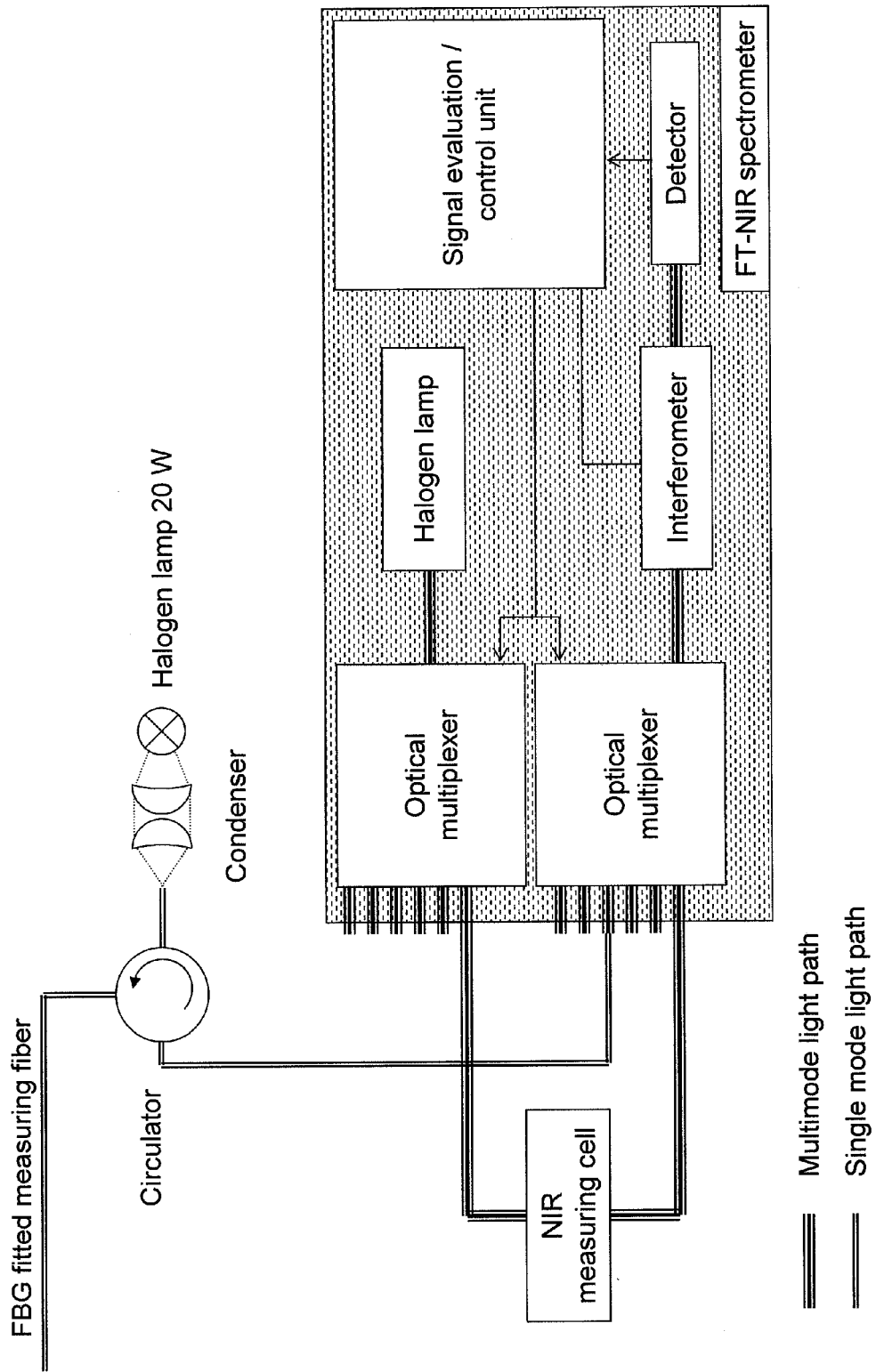
FIG. 7 Exemplary configuration with a halogen lamp as light source for FBG spectroscopy.
Figure 9:
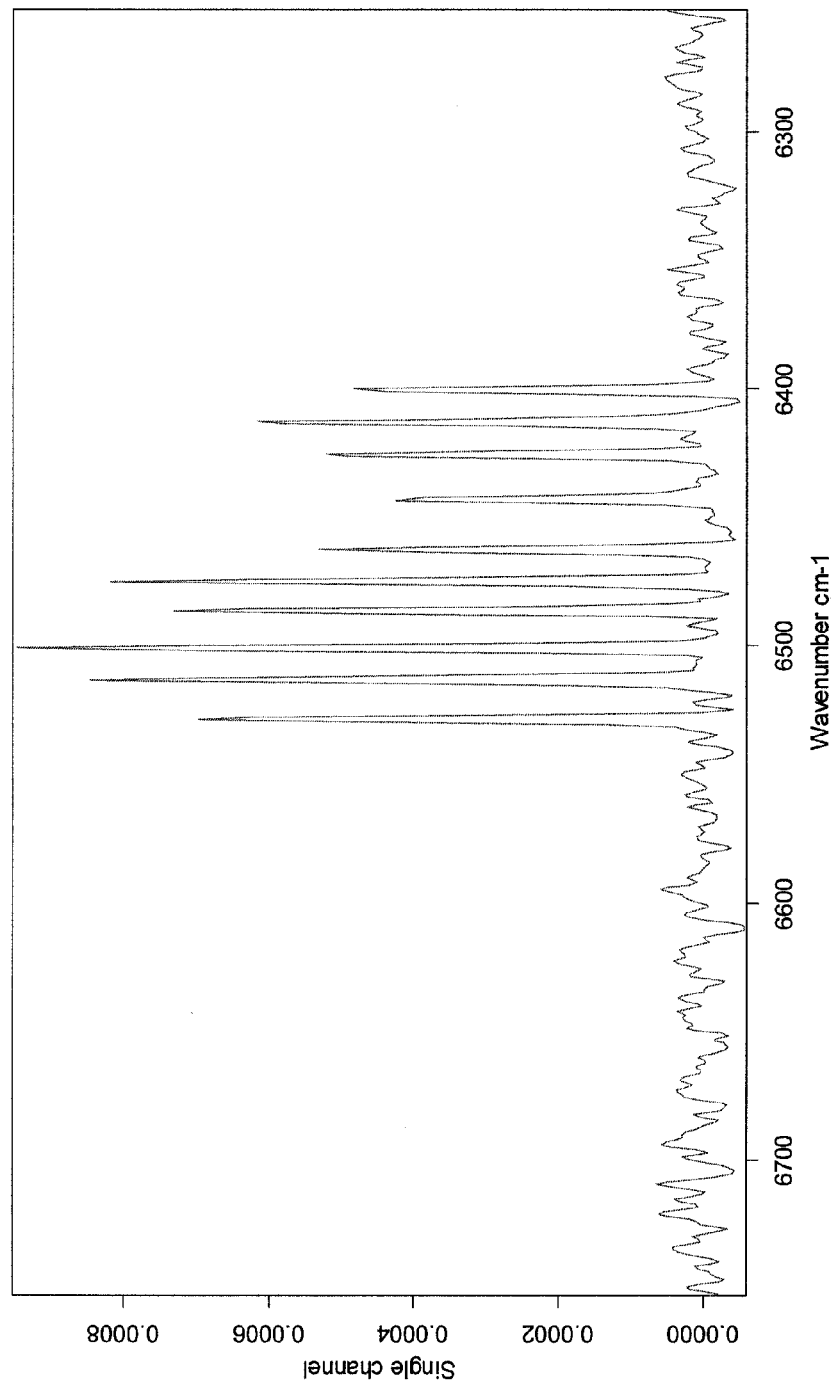
FIG. 9 Reflection spectrum of a glass fiber fitted with ten fiber Bragg gratings, recorded with the aid of a Bruker-Duplex FT-NIR spectrometer with the use of a halogen lamp as light source.

In FIG. 7, the arrangement according to FIG. 6 is modified such that a halogen lamp with condenser was used for illuminating the glass fiber fitted with fiber Bragg gratings. FIG. 9 shows the spectrum of the fiber Bragg grating measured therewith.

The invention claimed is:

1. A spectroscopic arrangement comprising
at least one light source for FBG fibers and a NIR measuring cell,
at least one optical multiplexer for connecting one or more measuring sections to an interferometer,
at least one FBG fiber and at least one glass fiber for NIR spectroscopy,
the interferometer, a detector and a signal evaluation/control unit for a machine-aided combination of near-infrared spectroscopy for determining material concentration with the spectroscopy on glass fibers fitted with fiber Bragg gratings for temperature and/or temperature profile measurement,
wherein the interferometer is arranged between an output of the one or more measuring sections and the detector.

2. The spectroscopic arrangement according to claim 1, wherein at least one separate light source is connected to each measuring section.

3. The spectroscopic arrangement according to claim 1, wherein the temporal sequence of the measuring sections to be examined spectroscopically is freely selected by the equipment controller.

4. The spectroscopic arrangement according to claim 1, wherein the spectroscopy is carried out in transmission on the glass fibers fitted with fiber Bragg gratings.

5. The spectroscopic arrangement according to claim 1, wherein one of SLEDs, ELEDs or incandescent lamps is used as light sources for the spectroscopy on glass fibers fitted with fiber Bragg gratings.

6. The spectroscopic arrangement according to claim 1, wherein a number of light sources are alternately spectrally combined for the spectroscopy on glass fibers fitted with fiber Bragg gratings.

7. The spectroscopic arrangement according to claim 1, wherein a common data path to a process control system is used for the measurement of material concentrations and temperature and/or temperature profiles.

8. A method for determining material concentrations and temperature and/or temperature profiles, providing the step of
providing a spectroscopic arrangement
providing at least one light source for FBG fibers and a NIR measuring cell,
providing at least one optical multiplexer for connecting one or more measuring sections to an interferometer,
providing at least one FBG fiber and at least one glass fiber for NIR spectroscopy,
providing the interferometer, a detector and a signal evaluation/control unit for a machine-aided combination of near-infrared spectroscopy for determining material concentration with the spectroscopy on glass fibers fitted with fiber Bragg gratings for temperature and/or temperature profile measurement,
wherein the interferometer is arranged between an output of the one or more measuring sections and the detector.

* * * * *